US010429298B2

(12) United States Patent
Vauclin et al.

(10) Patent No.: US 10,429,298 B2
(45) Date of Patent: Oct. 1, 2019

(54) METHOD FOR DETERMINING THE REFLECTANCE OF AN OBJECT AND ASSOCIATED DEVICE

(71) Applicant: COLOR GRAIL RESEARCH, Le Plessis-Robinson (FR)

(72) Inventors: Rémi Vauclin, Sannois (FR); Franck Hennebelle, Le Plessis Robinson (FR)

(73) Assignee: COLOR GRAIL RESEARCH, Le Plessis-Robinson (FR)

( * ) Notice: Subject to any disclaimer, the term of this patent is extended or adjusted under 35 U.S.C. 154(b) by 0 days.

(21) Appl. No.: 15/764,603

(22) PCT Filed: Sep. 30, 2016

(86) PCT No.: PCT/EP2016/073466
§ 371 (c)(1),
(2) Date: Mar. 29, 2018

(87) PCT Pub. No.: WO2017/055580
PCT Pub. Date: Apr. 6, 2017

(65) Prior Publication Data
US 2018/0284020 A1    Oct. 4, 2018

(30) Foreign Application Priority Data

Sep. 30, 2015 (FR) .................................. 15 59287
Sep. 30, 2015 (FR) .................................. 15 59309

(51) Int. Cl.
*G01N 21/55*    (2014.01)
*G01J 3/10*    (2006.01)
(Continued)

(52) U.S. Cl.
CPC ................ *G01N 21/55* (2013.01); *G01J 3/10* (2013.01); *G01N 21/31* (2013.01);
(Continued)

(58) Field of Classification Search
CPC .................. G01N 21/55; G01N 21/31; G01N 2201/0696; G01N 2201/0616; G01N 2201/0221
(Continued)

(56) References Cited

U.S. PATENT DOCUMENTS 6,310,626 B1    10/2001    Walker et al.
9,671,329 B2    6/2017    Hennebelle
(Continued)

FOREIGN PATENT DOCUMENTS

EP    1 032 194 A2    8/2000
FR    2 821 671 A1    9/2002
(Continued)

OTHER PUBLICATIONS

Rodgers et al., "Textile Technology—Portable Color Spectrophotometer Measurements of Cotton Color in Remote Locations", The Journal of Cotton Science, 2013, pp. 202-211, vol. 17, No. 3.
(Continued)

*Primary Examiner* — Hoa Q Pham
(74) *Attorney, Agent, or Firm* — Young & Thompson

(57) ABSTRACT

Disclosed is a method for determining the reflectance of an object, the method including a step of solving an equation having several unknowns, the equation being obtained from formed images, the reflectance of the object and the illumination of the external light source being two unknowns of the equation. The step of solving the equation includes: calculating solution points of the equation, interpolating the calculated points by way of an interpolation function, and using at least one of the following approximations to solve the equation: a first approximation according to which each image is derived from the emission of a separate light flash, a second approximation according to which the interpolation function determines the stability points of the equation.

13 Claims, 6 Drawing Sheets

(51) Int. Cl.
*G01N 21/31* (2006.01)
*G01J 3/42* (2006.01)

(52) U.S. Cl.
CPC .............................. *G01J 2003/425* (2013.01);
*G01N 2201/0221* (2013.01); *G01N 2201/0616*
(2013.01); *G01N 2201/0696* (2013.01)

(58) Field of Classification Search
USPC ................................. 356/445–448, 601–623
See application file for complete search history.

(56) References Cited

U.S. PATENT DOCUMENTS

| | | | | |
|---|---|---|---|---|
| 2002/0171842 | A1* | 11/2002 | Dicarlo | G01N 21/55 356/445 |
| 2007/0268481 | A1* | 11/2007 | Raskar | G01J 1/42 356/218 |
| 2011/0047867 | A1* | 3/2011 | Holland | G01J 3/10 47/1.5 |
| 2011/0261355 | A1 | 10/2011 | Hannel et al. | |
| 2014/0146304 | A1* | 5/2014 | Almalki | G01N 21/55 356/51 |

FOREIGN PATENT DOCUMENTS

| | | |
|---|---|---|
| FR | 2 870 337 A1 | 11/2005 |
| FR | 2 987 120 A1 | 8/2016 |
| WO | 2013/120956 A1 | 8/2013 |

OTHER PUBLICATIONS

FR Search Report, dated Aug. 8, 2016, from corresponding FR application No. 15 59287.
FR Search Report, dated Aug. 11, 2016, from corresponding FR application No. 15 59309.
International Search Report, dated Dec. 23, 2016, from corresponding PCT Application No. PCT/EP2016/073466.

* cited by examiner

METHOD FOR DETERMINING THE REFLECTANCE OF AN OBJECT AND ASSOCIATED DEVICE

FIELD OF THE INVENTION

The present invention relates to a method for determining the reflectance of an object and a device for determining the reflectance of an object.

BACKGROUND OF THE INVENTION

Document WO 2013/120956 A1 describes a method for measuring the uniform diffuse reflectance at least at one point of an object using a device comprising a means able to emit color illuminants expressed in the form of light flows and an electronic color image sensor, and a device comprising a means able to emit color illuminants in the form of light flows of colors and an electronic color image sensor, to measure the uniform diffuse reflectance at least at one point of an object placed in a zone located in the illumination field of said means able to emit colors and being located in the field of view of the electronic color image sensor and being subject to an outside illuminant in the form of a constant and unknown surrounding outside light flow.

To determine the reflectance of an object, it is known to use specialized high precision devices, such as diffraction spectrometers or double parallel photoreceptor spectrometers.

However, such devices are costly and difficult to use for nonspecialized operators.

SUMMARY OF THE INVENTION

There is therefore a need for a method for determining the reflectance that is reliable and easy to implement.

To that end, a method for determining the reflectance of an object is proposed, the method comprising the following steps:
  illuminating the object using an outside illuminant having an unknown and variable illumination,
  emitting at least one flash of light illuminating the object, each flash of light being emitted by a source and having a known illumination in a wavelength range,
  collecting the wave reflected by the object to form at least one image on a sensor,
  obtaining an equation with several unknowns, the equation being obtained from formed images, the reflectance of the object and the illumination of the outside illuminant being two unknowns of the equation,
  solving the equation,
the step for solving the equation comprising
  calculating solution points of the equation,
  interpolating points calculated by an interpolation function, and
  using at least one of the following approximations to solve the equation:
    a first approximation according to which each image is derived from the emission of a separate flash of light,
    a second approximation according to which the interpolation function determines the stability points of the equation, and
    a third approximation according to which the illumination of the outside illuminant at the moment of emission of a flash of light is equal to the illumination of the outside illuminant at a preceding moment.

Such a method for determining the reflectance $\rho$ of an object is easy to carry out and makes it possible to obtain a reliable model of the actual reflectance $\rho$ of the object even with a variable outside illuminant. Such an implementation makes it possible to reduce the calculation time, while retaining the precision of the method.

According to specific embodiments, the method for determining the reflectance of an object comprises one or more of the following features, considered alone or according to any technically possible combination:
  the source and the sensor are positioned on a same apparatus.
  a plurality of flashes of light are emitted, each flash having a maximum wavelength illumination, the collecting step being carried out for each flash of light emitted and at least two flashes of light have a maximum illumination separated by at least 20 nanometers.
  the collecting step is carried out several times for a same flash of light, the obtained equation being an overdetermined system of equations, the solving step being carried out for a plurality of determined equation systems by using the first approximation to obtain a plurality of reflectance functions, the method further comprising calculating the reflectance of the object by calculating a mean of the plurality of reflectance functions.
  the second approximation is used during the step for solving the equation and in which the interpolation function is a weighted combination of base functions sealed by a finite number of interpolation points, in particular cubic splines, each interpolation point being a stability point of the equation.
  a plurality of flashes of light are emitted, each flash having a maximum wavelength illumination, the collecting step being carried out for each flash of light emitted. The interpolation points verify at least the following property: the number of interpolation points is equal to the number of flashes.
  the third approximation is used and in which the method comprises a step for taking a reference image by collecting the wave reflected by the object to form at least one image on a sensor in the absence of flash emitted by the source.
  the step for solving the equation comprises an operation for subtraction of a reference equation to obtain a simplified equation, the reference equation being obtained from the reference image.
  the method further comprises the following steps:
    estimating a variation time interval for the illumination of the outside illuminant,
    from the estimated variation time interval, determining the frequency at which the step for taking a reference image is to be reiterated in order for the first approximation to remain valid.
  the method is a method for measuring the uniform diffuse reflectance $\rho^{OBJ}(\lambda)$ at least at one point of an object using a device comprising a means able to emit color illuminants expressed in the form of light flows and an electronic color image sensor, characterized in that it comprises the following steps:
    placing said object in a zone located in the illumination field of said means able to emit color illuminants in the form of colored light flows and located in the field of view of said electronic color image sensor, said object also being subject to an outside illuminant in the form of a surrounding outside light flow $I^{ext}(\lambda)$ unknown and constant, where $\lambda$ designates the wavelength, emission by said means of a series of N illuminants $S^{SOURCE}(\lambda)_i$ (with N a natural integer greater than one, i varying from 1 to N and $\lambda$, the wavelength), $S^{SOURCE}(\lambda)_i$ being known as a function of the input parameters of said means able to emit colored light flows, capturing by said electronic color image sensor the reflected light flow at least at one point of said object and entering the sensor, said light flow being $E^{capteur}(\lambda)_i$, with N a natural integer strictly greater than two, i varying from 1 to N and $\lambda$ the wavelength, and obtaining N equations "$E_i$":

$$E^{capteur}(\lambda)_i = \rho^{OBJ}(\lambda) * (I^{ext}(\lambda) + S^{SOURCE}(\lambda)_i)$$

due to the additive nature of the wave light and by definition of the uniform diffuse reflectance $\rho^{OBJ}(\lambda)$ at least at one point of the object (30); and determining, via said device, two continuous unknown functions $\rho^{OBJ}(\lambda)$ and $I^{ext}(\lambda)$ by solving the system of N equations $E_i$:

by integrating each equation $E_i$ on the intersection of the source and sensor spectrums, by using reference $b_j$ to denote each sensitivity in the selected colorimetric base, each equation $E_i$ then generating a set of "$E_i$ integrated" equations:

$$\int E^{capteur}(\lambda)_i * b_j(\lambda) * d\lambda = \int \rho^{OBJ}(\lambda) * (I^{ext}(\lambda) + S^{SOURCE}(\lambda)_i) * b_j(\lambda) * d\lambda$$

by calculating the numerical value corresponding to the left term of the integrated equations $E_i$ using output parameters from the digital image sensor; and by expressing the two continuous unknown functions $\rho^{OBJ}(\lambda)$ and $I^{ext}(\lambda)$ using a finite number of interpolation points $(\lambda_i, y_i)$ connected by at least one interpolation function $s(\lambda)$ to retain the continuous nature of said continuous unknown functions $\rho^{OBJ}(\lambda)$ and $I^{ext}(\lambda)$ the $\lambda_i$ being wavelengths chosen in the intersection of the source and sensor spectrums and being input parameters of the method, chosen to minimize the number of interpolation points with a given precision; and by looking for the parameters yi of the functions $\rho^{OBJ}(\lambda)$ and $I^{ext}(\lambda)$ that minimize the system of least squares $\|A*X-B\|_2$ resulting from the integrated equations $E_i$.

the method further comprises a step for determining the value of the outside illuminant $I^{ext}(\lambda)$.

the method further comprises a step for transcribing the uniform diffuse reflectance function $\rho^{OBJ}(\lambda)$ at least at one point of the object in CIE XYZ coordinates for a given illuminant.

the number of flashes is of the same order of magnitude as the number of interpolation points to determine the values of the uniform diffuse reflectance $\rho^{OBJ}(\lambda)$ at least at one point of the object and of the outside illuminant $I^{ext}(\lambda)$.

the method comprises a step for determining the values of the uniform diffuse reflectance $\rho^{OBJ}(\lambda)$ at least at one point of the object and of the outside illuminant $I^{ext}(\lambda)$ in several spectral bands.

the method is implemented to take spectrometric photographs of objects and to perform chromatic adaptations (white balancing) at will.

the method is implemented to measure the color of an element comprised in the following group: materials, solids, liquids, gases, paints, wallpapers, graphics, textiles, plastics, woods, metals, soils, minerals, plants and foods.

the method is implemented to measure colors for medical or cosmetic purposes on humans and the living organisms of at least one element comprised in the following group: skin, pimples, beauty marks, scalp, hair, makeup and teeth.

the method is implemented for the use of color barcodes, with one or more dimensions.

the method is implemented with the aim of assisting colorblind and/or blind persons.

The present description also relates to the device for determining the reflectance of an object, the object being illuminated by an outside illuminant having an unknown and variable illumination, the device comprising:

a source, able to emit at least one flash of light illuminating the object, each flash of light emitted by the source having a known illumination in a wavelength range, a sensor, able to collect the wave reflected by the object to form at least one image, a processing unit, able to carry out the following steps:
obtaining an equation with several unknowns, the equation being obtained from formed images, the reflectance of the object and the illumination of the outside illuminant being two unknowns of the equation,
solving the equation, the step for solving the equation comprising:
calculating solution points of the equation,
interpolating points calculated by an interpolation function, and
using at least one of the following approximations to solve the equation:
a first approximation according to which each image is derived from the emission of a separate flash of light,
a second approximation according to which the interpolation function determines the stability points of the equation, and
a third approximation according to which the illumination of the outside illuminant at the moment of emission of a flash of light is equal to the illumination of the outside illuminant at a preceding moment.

According to specific embodiments, the device for determining the reflectance of an object comprises one or more of the following features, considered alone or according to any technically possible combination:

the sensor and the source are positioned on a same apparatus.

the source is a light screen or a set of light-emitting diodes.

the sensor is chosen from a group made up of a photographic camera, a camera, a multichannel imager and a hyperspectral imager.

the apparatus is a smart phone.

said device implements a set of light sources to emit the color flashes and an electronic image sensor to capture the light reflected by the target object.

said device is a photographic camera or a camera with integrated or removable flash.

said device implements waveguides to cause the emission and perception of color flashes to pass through.

said device is implemented to take spectrometric photographs of objects and to perform chromatic adaptations (white balancing) at will.

said device is implemented to measure the color of an element comprised in the following group: materials, solids, liquids, gases, paints, wallpapers, graphics, textiles, plastics, woods, metals, soils, minerals, plants and foods.

said device is implemented to measure colors for medical or cosmetic purposes on humans and the living organisms of at least one element comprised in the following group: skin, pimples, beauty marks, scalp, hair, makeup and teeth.

said device is implemented for the use of color barcodes, with one or more dimensions, and said device is implemented with the aim of assisting colorblind and/or blind persons.

the device further includes a means able to emit color illuminants in the form of light flows of colors and an electronic color image sensor, to measure the uniform diffuse reflectance $\rho^{OBJ}(\lambda)$ at least at one point of an object placed in a zone located in the illumination field of said means able to emit colors and being located in the field of view of the electronic color image sensor and being subject to an outside illuminant in the form of a constant and unknown surrounding outside light flow denoted $I^{ext}(\lambda)$. The device also comprises means for:

emitting a series of N illuminants $S^{SOURCE}(\lambda)_i$ (with N a natural integer greater than one, i varying from 1 to N and λ, the wavelength), $S^{SOURCE}(\lambda)_i$ being known as a function of the input parameters of said means able to emit colored light flows, capturing by said electronic color image sensor the reflected light flow at least at one point of said object and entering the sensor, said light flow being $E^{capteur}(\lambda)_i$, with N a natural integer strictly greater than one, i varying from 1 to N and λ the wavelength, and obtaining N equations "$E_i$":

$$E^{capteur}(\lambda)_i = \rho^{OBJ}(\lambda) * (I^{ext}(\lambda) + S^{SOURCE}(\lambda)_i)$$

due to the additive nature of the wave light and by definition of the uniform diffuse reflectance $\rho^{OBJ}(\lambda)$ at least at one point of the object; and determining the two continuous unknown functions $\rho^{OBJ}(\lambda)$ and $I^{ext}(\lambda)$ by solving the system of N equations $E_i$:

by integrating each equation $E_i$ on the intersection of the source and sensor spectrums, by using reference $b_j$ to denote each sensitivity in the selected colorimetric base, each equation $E_i$ then generating a set of "$E_i$ integrated" equations:

$$\int E^{capteur}(\lambda)_i * b_j(\lambda) * d\lambda = \int \rho^{OBJ}(\lambda) * (I^{ext}(\lambda) + S^{SOURCE}(\lambda)_i) * b_j(\lambda) * d\lambda$$

by calculating the numerical value corresponding to the left term of the integrated equations $E_i$ using output parameters from the digital image sensor; and by expressing the two continuous unknown functions $\rho^{OBJ}(\lambda)$ and $I^{ext}(\lambda)$ using a finite number of interpolation points $(\lambda_i, y_i)$ connected by at least one interpolation function $s(\lambda)$ to retain the continuous nature of said continuous unknown functions $\rho^{OBJ}(\lambda)$ and $I^{ext}(\lambda)$ the $\lambda_i$ being wavelengths chosen in the intersection of the source and sensor spectrums and being input parameters of the method, chosen to minimize the number of interpolation points with a given precision; and by looking for the parameters yi of the functions $\rho^{OBJ}(\lambda)$ and $I^{ext}(\lambda)$ that minimize the system of least squares $\|A*X-B\|_2$ resulting from the integrated equations $E_i$.

BRIEF DESCRIPTION OF THE DRAWINGS

Other features and advantages of the invention will appear upon reading the following description of embodiments of the invention, provided as an example only and in reference to the drawings, which are.

DETAILED DESCRIPTION OF THE PREFERRED EMBODIMENTS

Figure 1:
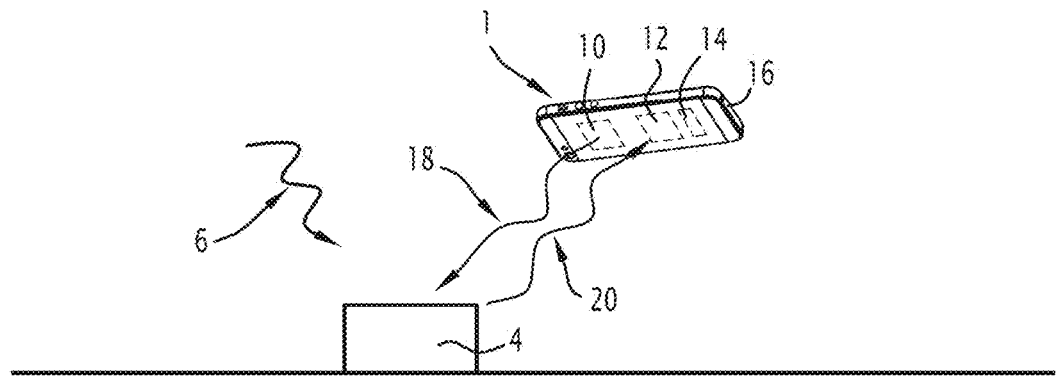
FIG. 1, a diagram of a device for determining the reflectance of an object.

A device 1 for determining the reflectance of an object 4, an object 4 and an outside illuminant 6 are shown in FIG. 1.

The device 1 for determining the reflectance of an object 4 comprises a source 10, a sensor 12 and a processing unit 14.

Figure 2:
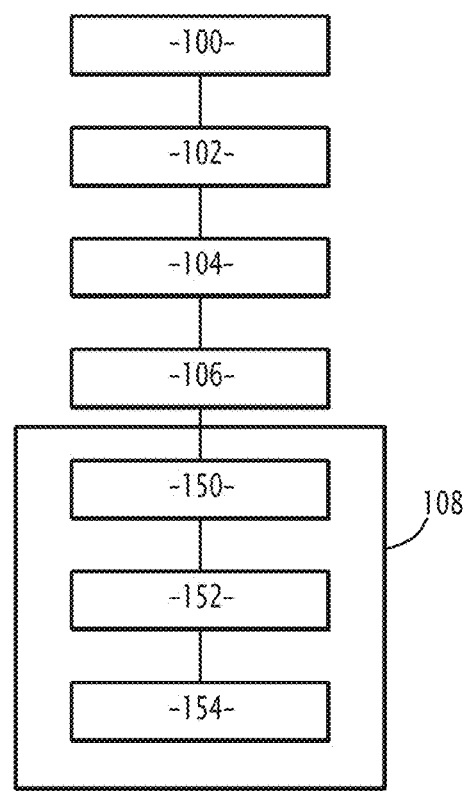
FIG. 2, a flowchart of a first example of the implementation of a method for determining the reflectance of an object, FIG. 3, a graphic representation of a spectrum for several light flashes, FIG. 4, a flowchart of a second example of the implementation of a method for determining the reflectance of an object, FIG. 5, a graphic representation of the error of the determined reflectance relative to an actual reflectance, for several determinations, FIG. 6, a graphic representation of the error of the determined reflectance relative to the actual reflectance, FIG. 7, a graphic representation of several determined reflectances and the actual reflectance, FIG. 8, a graphic representation of the reflectance determined by carrying out a method of the state of the art and the actual reflectance, FIG. 9, a graphic representation of the determined reflectance for an example of implementation of the determination method and the actual reflectance, and FIG. 10, a flowchart of a third example of implementation of a method for determining the reflectance of an object.

The determination device 1 is able to carry out a method for determining the reflectance of an object 4, an example embodiment of which is shown in FIG. 2.

The actual reflectance of an object, denoted $\rho_{réelle}$, a function $\rho_{réelle}(\lambda)$ of the wavelength, denoted λ.

The reflectance provides information on the color of the object 4 in the chromatic sense. The reflectance of the object 4 depends on the material of the reflection surface of the object 4.

The reflectance of an object 4 is defined as the ratio between the illumination received by the object 4 and the luminance reflected by the object 4.

The luminance is a property corresponding to the visual sensation of brightness of a surface. The luminance received by the object 4 is defined as the quotient of the light intensity received by the object 4 by the area of the visible surface of the object 4. The luminance reflected by the object 4 is defined as the quotient of the light intensity reflected by the object 4 by the area of the visible surface of the object 4. The visible surface is the projection of the area of the object 4 perpendicular to an observation direction.

The illumination of the object 4 is known from the luminance received by the object 4 and the observation geometry.

In the determination method, the surface of the object 4 is considered a Lambertian surface. A Lambertian surface is a surface where the luminance is independent of the observation direction. The specular component of the surface of the object 4, i.e., its shiny appearance, is presumed to be negligible or is not collected by the device 1 owing to an appropriate geometric arrangement between the light source 10, the object 4 and the sensor 12.

The illumination of the object 4 corresponds to a light flow received by a surface unit.

The determination of the reflectance consists of finding a determined reflectance, denoted ρ, that is as close as possible according to a standard, to the actual reflectance $\rho_{réelle}$ of an object 4 over a range of wavelengths. The range of wavelengths depends on the source 10 and the sensor 12 of the determination device 1. For example, the reflectance is determined over a range of wavelengths in the visible domain.

The determined reflectance is denoted p in the rest of the description.

The reflectance ρ determined by the determination method is advantageously close to the actual reflectance $\rho_{réelle}$ over a range of wavelengths as described hereinafter.

An error F of the determined reflectance ρ relative to the actual reflectance $\rho_{réelle}$ is a function of the wavelength defined from the standard deviation between the actual reflectance $\rho_{réelle}$ and the determined reflectance p.

The error F is a null function if the determined reflectance ρ is equal to the actual reflectance $\rho_{réelle}$ for all of the wavelengths. The higher the error F is, the more this indicates that the deviation between the determined reflectance ρ and the actual reflectance $\rho_{réelle}$ is big.

It is understood that the method for determining the reflectance ρ and the device 1 for determining the reflectance ρ of an object 4 are applicable to determine the reflectance ρ of any object 4.

For example, the object 4 is part of a patient's skin, a color barcode, a paint, a cosmetic product such as a foundation, or the like.

The object 4 is positioned in an environment comprising an unknown number of illumination sources of the object 4. The set of sources eliminating the object 4 may vary during the method for determining the reflectance of the object 4. Furthermore, the illumination, coming from different sources illuminating the object 4 and separate from the source 10 of the determination device 1, may fluctuate during the method for determining the reflectance of the object 4.

For example, an object 4, placed in an illuminated window, is illuminated by the daylight passing through the window and by the bulbs inside the store, with unknown and variable light flows.

The set of sources illuminating the object 4 and separate from the source 10 of the determination device 1 is represented by an outside illuminant 6 having an unknown and variable illumination as a function of time, denoted I.

The illumination I of the outside illuminant 6 depends on the set of fluctuations of the illumination sources of the object 4 separate from the source of the device 10 illuminating the object 4.

Under particular conditions, the illumination I of the outside illuminant 6 is fixed. At each moment, the object 4 is illuminated by the outside illuminant 6, and optionally by the source 10. The illumination received by the object 4 is the sum of the illumination coming from the source 10 of the determination device 1 with the illumination from the outside illuminant 6.

At each moment t, the object 4 illuminated by the outside illuminant 6, and optionally by the source 10, reflects a wave 20 depending on the actual reflectance $\rho_{réelle}$ of the object 4.

In the embodiment of the determination device 1 shown in FIG. 1, the sensor 12 and the source 10 are positioned on a same apparatus 16.

For example, the apparatus 16 is a touch-sensitive tablet, a mobile telephone, a smart phone, or the like.

The source 10 is able to emit at least one flash of light 18 illuminating the object 4.

For example, the source 10 is a light screen or a set of bulbs. For example, the set of bulbs is a set of light-emitting diodes (LEDs).

A flash of light 18 is a light flow emitted during a short time interval. For example, the emission time interval is comprised between 1 ms (millisecond) and 2 s (seconds). The emission time interval depends on the characteristics of the source 10 and the sensor 12.

The light flow of the flash of light 18 has an emission intensity as a function of the wavelength depending on the source 10.

The source 10 is able to emit each flash 18 in the visible domain. This means that for each flash 18, the emission intensity is above a threshold for perception by the human eye for at least one wavelength comprised between 380 nm (nanometers) and 800 nm. Alternatively or additionally, the source 10 is able to emit in the infrared domain, in particular at a wavelength comprised between 800 nm and 1000 nm.

Each flash i of light 18 emitted by the source 10 has an illumination of the object 4, denoted $E_i$ and depending on the wavelength. For each flash i, the illumination $E_i$ in a range of wavelengths is a known characteristic of the source 10. The characteristics of the source 10 are kept in a memory.

The characteristics of the source 10 are determined before carrying out the determination method.

The range of wavelengths is delimited by a minimum wavelength value $\lambda_{min}$ and a maximum wavelength value $\lambda_{max}$. Each wavelength of the range of wavelengths is comprised between the minimum wavelength value $\lambda_{min}$ and the maximum wavelength value $\lambda_{max}$. The range of wavelengths depends on the source 10 and the sensor 12 used to emit and receive the flashes 18.

The source 10 is able to emit flashes of light 18. The illumination $E_i$ of a flash i has a maximum illumination in the range of wavelengths. The maximum illumination is a global maximum of the illumination $E_i$ as a function of the wavelength. The maximum illumination of a flash i is a wavelength denoted $\lambda_i$.

The moment where the source 10 emits a flash is called emission moment. Each emission moment of a flash i is denoted $t_i$. The emission moment $t_i$ of each flash i is a datum kept in a memory.

The source 10 is able to emit several flashes 18 successively. The time interval between two emission moments $t_i$, $t_j$ of successive flashes i, j is for example comprised between 1 ms and 2 s.

The source 10 is able to emit several flashes 18 of different colors, i.e., having different spectrums. The source 10 is able to emit at least two emitted flashes i, j of light 18 having a maximum illumination at wavelengths $\lambda_i$ and $\lambda_j$ separated by at least 20 nanometers (nm).

Figure 3:
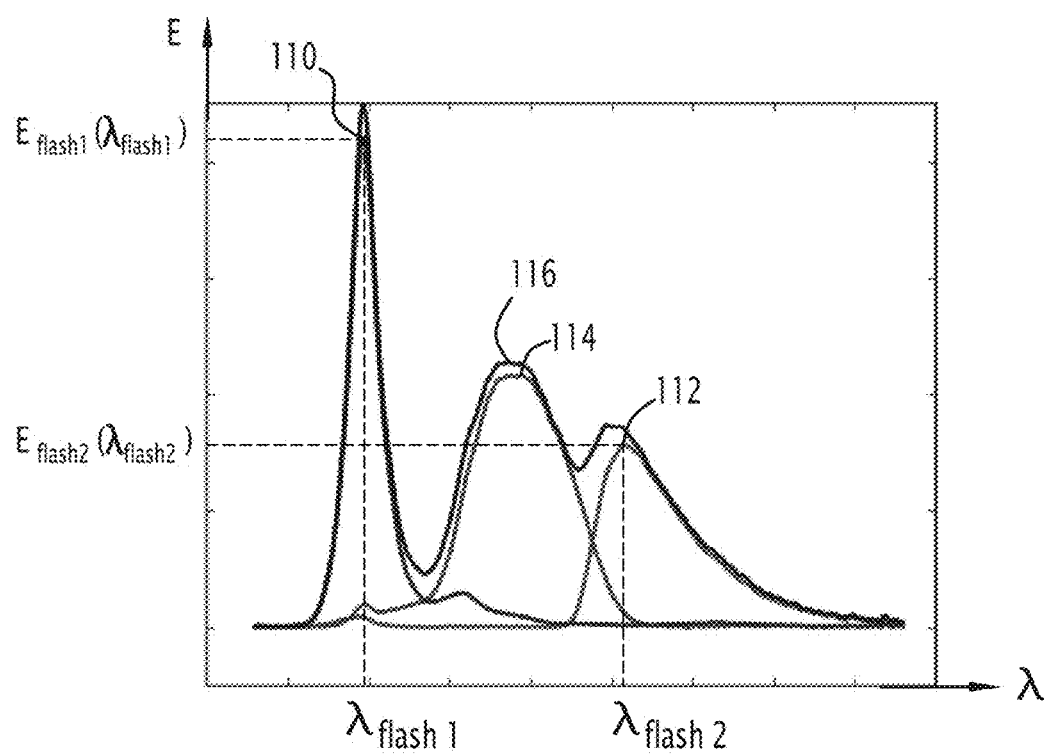

In one example, the source 10 is able to emit four flashes: a blue flash, a red flash, a green flash and a white flash. In FIG. 3, each curve 110, 112, 114, 116 shows the illumination of the object 4 by the source 10 as a function of the wavelength, without outside illuminant 6, for a respective flash. In FIG. 3, the blue flash "flash1", corresponding to the first curve 110, has maximum illumination at the value $\lambda_{flash1}$, while the red flash "flash2", corresponding to the second curve, denoted 112, has a maximum illumination at the value $\lambda_{flash2}$.

The sensor 12 is able to collect the wave 20 reflected by the object 4 to form at least one image, For example, the sensor 12 is a photographic camera or a camera.

The sensor 12 is able to detect light intensities in the emitting wavelength range of the source 10.

The sensitivity of the sensor 12 in the wavelength range is a characteristic of the sensor 12 stored in a memory. The characteristics of the sensor 12 are determined before carrying out the determination method.

Furthermore, the sensitive part of the sensor 12 is not oriented toward the source 10. This makes it possible for the collection of the reflected wave 20 not to be disrupted by the direct light from the flash of light 18 emitted by the source 10.

The formed image contains colorimetric data. For each formed image k, the data from the image is denoted $B_k$.

The moment where the sensor 12 provides an image is called collection moment. Each collection moment of an image k is denoted $t_k$. Likewise, the collection moment $t_k$ of each image k is a datum kept in a memory.

The sensor 12 is able to collect several images successively. The sensor 12 is fast, i.e., the sensor 12 is able to form images at close collection moments. The time interval between two collection moments $t_k$, $t_l$ of successive flash images k, l is for example comprised between 1 ms and 2 s.

In the embodiment of the device 1 shown in FIG. 1, the processing unit 14 is positioned on the apparatus 16 where the source 10 and the sensor 12 are positioned.

The processing unit 14 for example comprises processors and memories.

The processing unit 14 is able to process data. The processing unit 14 is additionally able to receive the data from the sensor 12 relative to each formed image k and each collection moment $t_k$ and the data from the source 10 relative to the illuminations $E_i$ of each flash i emitted and at the emission moments $t_i$.

The processing unit 14 is able to obtain an equation with several unknowns from the formed images. Hereinafter, the obtained equation is called the equation to be solved (1).

The reflectance ρ of the object 4 and the illumination I of the outer illuminant 6 are both unknowns of the equation to be solved (1).

Furthermore, the processing unit 14 is able to ensure that the equation to be solved (1) is solved.

The obtaining and solving of the equation to be solved (1) by the processing unit 14 are described in the continuation of the description.

The operation of the device 1 is now described in reference to FIG. 2, which is a flowchart of a first example of implementation of the method for determining the reflectance ρ of the object 4.

The method for determining the reflectance ρ comprises the following five steps: an illumination step 100, an emission step 102, a collection step 104, an obtaining step 106 and a solving step 108.

During the illumination step 100, at each moment denoted t, the object 4 is illuminated by the outside illuminant 6 having the illumination $I_t$.

The emission step 102 is carried out by the source 10 of the device 1.

During the emission step 102, the source 10 emits, at an emission moment $t_i$, a flash of light i illuminating the object 4.

In one preferred embodiment, during the emission step, the source 10 emits a plurality of flashes of light 18, each flash i being emitted at different emission moments $t_i$.

The emission moments $t_i$ and the illuminations $E_i$ of each emitted flash i of light 18 are sent to the processing unit 14.

The collection step 104 is carried out by the sensor 12 of the device 1.

During the collection step 104, the wave 20 reflected by the object 4 is collected to form at least one image at a collection moment on the sensor 12.

In one preferred embodiment, the collection step 104 is carried out for each emitted flash of light 18.

The data relative to the collection moments and the formed images are sent to the processing unit 14.

The processing unit 14 receives the data relative to the illuminations from the flashes, at the emission moments $t_i$, at the collection moments $t_k$ and at the images respectively formed from the source 10 and the sensor 12.

During the obtaining step 106, the equation to be solved (1) is obtained.

The obtaining step 106 is carried out by the processing unit 14.

The processing unit 14 converts each formed image into an equation.

For example, for each image k, the processing unit 14 determines whether the collection moment $t_k$ of the image k takes place at an emission moment of a flash.

Two cases are then possible.

In a first case, if the collection moment $t_i$ of an image i is an emission moment of a flash, the flash is denoted i, and the processing unit 14 obtains, from the image k, a first equation (2) linking the data $B_i$ from the formed image i to the reflectance ρ of the object 4.

The first equation (2) is then written in the following form in the case of a Lambertian surface:

$$B_i = K_1 * \int_{\lambda_{min}}^{\lambda_{max}} \rho(\lambda) * (E_i + I_{t_i})(\lambda) * b(\lambda) d\lambda$$

where:
$K_1$ is a first constant,
'*' designates the multiplication operation,
$\int_{\lambda_{min}}^{\lambda_{max}} f(\lambda) \, d\lambda$ designates the mathematical operation of integrating the function f on the variable λ in the interval $[\lambda_{min}, \lambda_{max}]$.

In a second case, if the collection moment $t_k$ of an image k is not a moment of emission of a flash, the processing unit 14 obtains, from the image k, a second equation (3) linking the data $B_k$ from the formed image k to the reflectance ρ of the object 4.

The second equation (3) is then written in the following form:

$$B_k = K_1 * \int_{\lambda_{min}}^{\lambda_{max}} \rho(\lambda) * I_{t_k}(\lambda) * b(\lambda) d\lambda$$

The processing unit 14 then extracts at least a first equation (2) or a second equation (3) to form the equation to be solved (1).

Advantageously, the equation to be solved (1) is a system of equations formed from first equations (2) and/or second equations (3) obtained for several formed images.

Equation (1) comprises N1 first equations (2) and N2 second equations (3), where N1 is a non-zero natural integer number of images formed at a collection moment that is an emission moment, and N2 is an integer number of images formed at a collection moment without flash emission.

The reflectance ρ of the object 4 and the illumination I of the outer illuminant 6 are both unknowns of the equation to be solved (1).

Below, it should be noted that the equation to be solved (1) can easily be represented in the form of a matricial equation, for a Lambertian surface.

At the end of the obtaining step 106, the equation to be solved (1) has been obtained using the processing unit 14.

The solving step 108 is then carried out by the processing unit 14.

The solving step 108 aims to solve the equation to be solved (1).

More specifically, during the solving step 108, the objective is to seek a reflectance ρ that is a solution to the equation to be solved (1).

In the general case, the solution for the equation to be solved (1) is highly sensitive to observation and/or modeling errors.

To limit the influence of errors on the solution p, it is proposed to combine three sub-steps during solving 108.

Consequently, according to the example embodiment of FIG. 2, the solving step 108 comprises three sub-steps.

The three sub-steps 150, 152, 154 of the solving 108 are carried out successively or in parallel by the processing unit 14.

During the first sub-step 150, the solution points of the equation to be solved (1) are calculated.

The processing unit 14 determines the number N of solution points P to be calculated. The number N of solution points P to be calculated is a non-zero natural integer.

Each solution point P to be calculated includes two coordinates, an x-coordinate and a y-coordinate.

According to the proposed example, the x-coordinates are first determined, then the associated y-coordinates are calculated.

The processing unit 14 determines N calculation wavelengths $\lambda_P$, each calculation wavelengths being the x-coordinate of a solution point.

Typically, for example, the number N of solution points P to be calculated is comprised between 4 and 10.

For example, the calculation wavelengths A are distributed uniformly over the range of wavelengths.

For each solution point P, the processing unit 14 calculates a reflectance value $\rho_P$ associated with the calculation wavelength $\lambda_P$ verifying the equation to be solved (1).

At the end of each solution point calculation sub-step 150, the processing unit 14 obtains a plurality of solution points P. Each solution point P comprises a reflectance value $\rho_P$ associated with the calculation wavelength $\lambda_P$ verifying the equation to be solved (1). During the second sub-step 152, an interpolation of the solution points P is carried out by the processing unit 14 using an interpolation function.

To carry out the second sub-step 152, the solution points P found during the first sub-step, the equation to be solved (1) and interpolation criteria are used.

The interpolation criteria define the type of interpolation functions to be examined.

According to one example, the interpolation criteria delimit a space around the equation to be solved (1) through which the points of the interpolation function must pass.

According to another example, the interpolation criteria limit the interpolation functions to be used.

Thus, in one particular case, the interpolation function is written in the form of a weighted combination of a finite number $n_p$ of base functions $\phi_k$.

For example, the interpolation function of the reflectance ρ is written in the following form:

$$\rho(\lambda) = \sum_{k=1}^{n_P} a_k * \phi_k(\lambda)$$

where the coefficients $\alpha_k$ are the weights associated with the base functions $\phi_k$.

During the second sub-step 152, the processing unit 14 determines the values of the weights $a_k$ and the forms of the base functions $\phi_k$.

For example, according to an interpolation criterion, the processing unit 14 defines each solution point P as an interpolation point.

Alternatively, other interpolation criteria are used during the second sub-step 152.

For example, according to one interpolation criterion, the base functions $\phi_k$ are sealed cubic splines. A cubic spline is a cubic polynomial defined by pieces. Each piece of the function is an order three polynomial function on each interval of wavelengths delimited by two interpolation points.

At the end of the second sub-step 152 for calculated points, the processing unit 14 obtains an interpolation function verifying the interpolation criteria.

The applicant has noted that this approach to solving the equation to be solved (1) sometimes leads to nonoptimal solutions.

To offset this problem, a third sub-step 154 is carried out at the same time as the first sub-step 150 or the second sub-step 152.

During this third sub-step 154, at least one approximation is used from among a first approximation and a second approximation. Alternatively or additionally, during this third sub-step 154, a third approximation is used by the processing unit 14.

According to the first approximation, each image is derived from the emission of a separate flash of light 18.

According to the second approximation, the interpolation function determines the stability points of the equation to be solved (1).

According to the third approximation, the illumination of the outside illuminant 6 at the moment of emission of a flash of light 18 is equal to the illumination of the outside illuminant 6 at a preceding moment.

At the end of the solving step 108, the processing unit 14 obtains a determined reflectance ρ.

The choice of approximations results from tests by the applicant of a plurality of possible approximations, these approximations having the advantage of making the method for determining the reflectance reliable and easy to carry out.

In each case, this results in a better determined reflectance ρ for a same calculation time.

Specific implementation modes for each of the approximations are outlined below.

Figure 4:
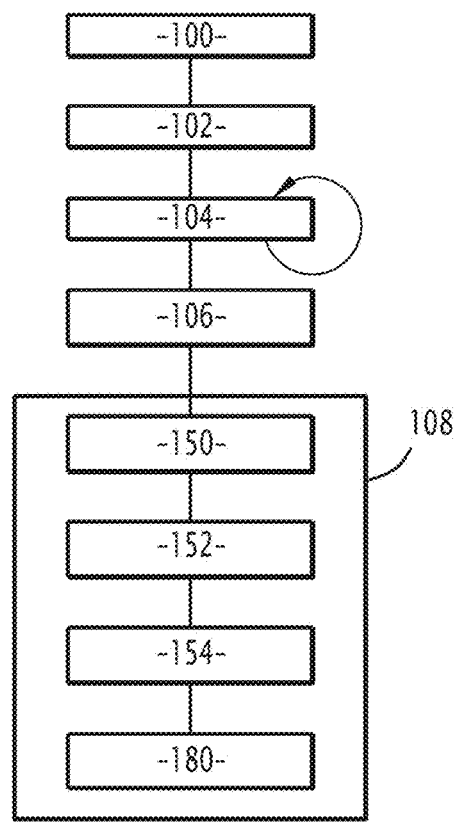

FIG. 4 is a flowchart illustrating one particular implementation of the method for determining the reflectance ρ when the first approximation is carried out.

The same steps as for the implementation of the method according to FIG. 2 are carried out.

The collection step 104 is carried out several times during a same flash of light.

By using the second approximation, it is considered that each image comes from a different flash.

As a result, in the obtaining step 106, the equation to be solved (1) includes more equations than unknowns. The equation to be solved (1) is therefore over-determined.

A plurality of sub-equations to be solved are then extracted from the equation to be solved (1). Each sub-equation to be solved forms an over-determined system.

In the solving step 108, each sub-equation is solved.

This results in a plurality of solution reflectances $\rho_{solution}$, each verifying the equation to be solved (1).

To determine the reflectance p, the mean of the plurality of solution reflectances $\rho_{solution}$ is calculated during a fourth sub-step 180 of the solving step 108.

For example, the calculation of the mean is carried out by an arithmetic mean calculation.

According to another example, the calculation of the mean is carried out by a quadratic mean calculation.

Such an embodiment is easy to carry out, since no additional flash is involved. In particular, while improving the precision, such a method is carried out with the same speed.

One particular implementation of the method for determining the reflectance $\rho$ will now be described when the second approximation is carried out.

In this example, it is proposed to reduce the number of interpolation points at the stability points of the equation.

According to the second approximation, the stability points of the equation are determined by the interpolation functions.

Preferably, the interpolation points are distributed over an interval of wavelengths, the interval of wavelengths for example being comprised between 380 nanometers and 780 nanometers in the case of a smart phone.

Figure 5:
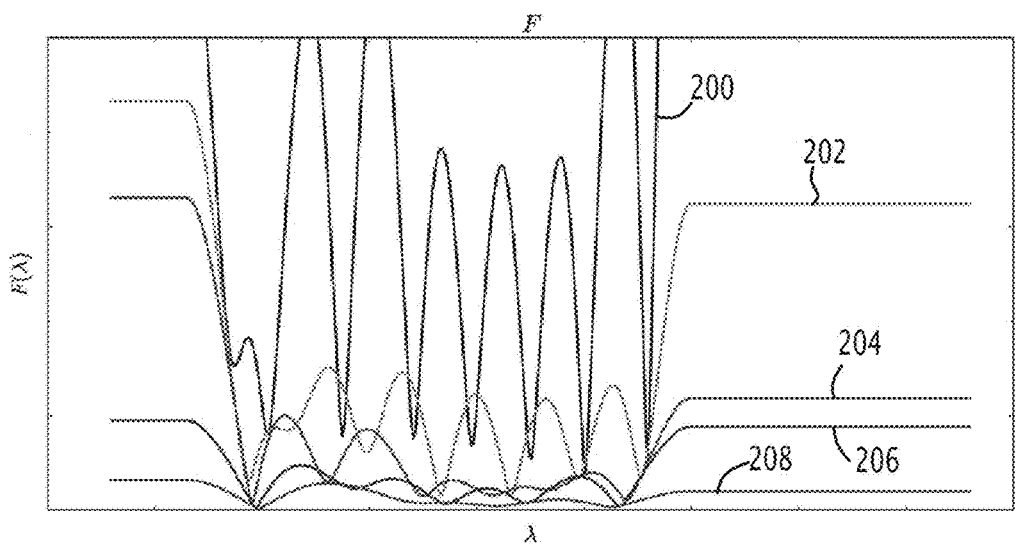
Figure 6:
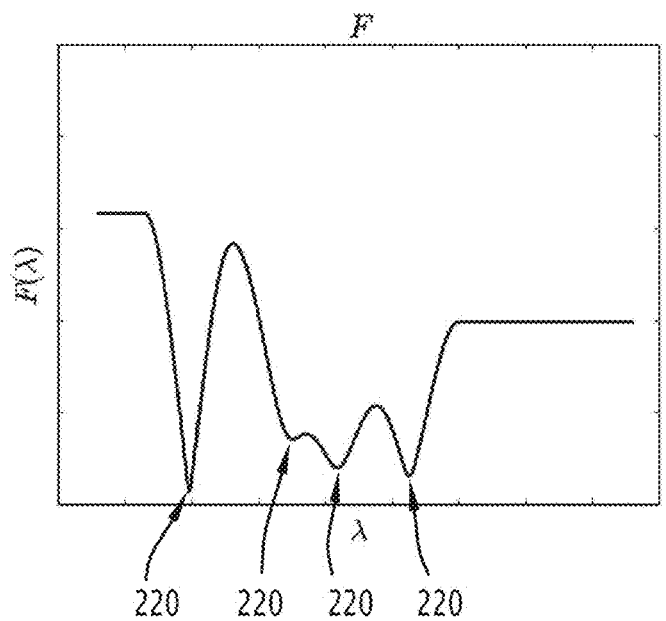
Figure 7:
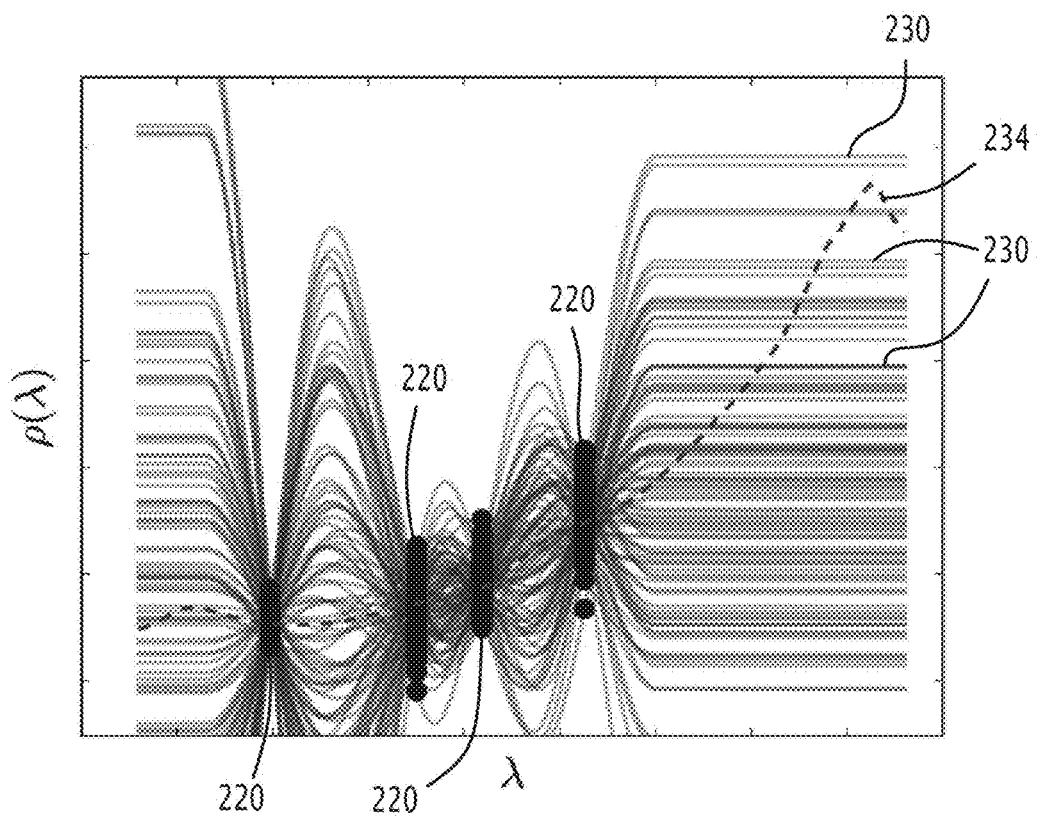

This second approximation is the result of work by the applicant illustrated by FIGS. 5 to 7.

A digital simulation of the error F was done for several simulations for determining the reflectance $\rho$.

In each simulation, different noise values are added to each image datum and each flash illumination. For example, the added noise is a Gaussian white noise. The noise is a model of the different defects at the source 10 or the sensor 12.

FIG. 5 shows the error function F as a function of the wavelength $\lambda$ according to the number of interpolation points selected for the interpolation function of $\rho(\lambda)$. Each curve 200, 202, 204, 206, 208 is respectively obtained for nine, eight, seven, six or five interpolation points.

The analysis of FIG. 5 shows that certain wavelengths are more sensitive to noise than others and that the higher the number of interpolation points is, i.e., the more basic functions the interpolation function comprises, the more sensitive the equation to be solved (1) is to instabilities.

FIG. 6 shows the error function F as a function of the wavelength for five interpolation points. The scale has been modified compared to the scale of FIG. 5 to show the details of the error function F. The error function F has 4 minima 220, which are stability points of the equation to be solved (1). The reflectance $\rho$ found for the wavelength minimizing the function F is less sensitive to noise.

In the example, the number of interpolation points is therefore equal to 4.

Advantageously, the number of interpolation points is equal to the number of flashes 18.

In FIG. 7, each curve 230 in solid lines represents the reflectance $\rho$ as a function of the wavelength for one hundred reflectances $\rho$ calculated with different noise simulations. The curve 234 in dotted lines represents the actual reflectance, known by other means. The stability points 220 are the points around which the deviation between the actual reflectance $\rho$ and the calculated reflectances $\rho$ is less significant than the deviation from the stability points 220.

These simulations illustrate the interest of the second approximation.

In all of the embodiments, the method for determining the reflectance $\rho$ of an object makes it possible to obtain a reliable model of the actual reflectance $\rho$ of the object even with a variable outside illuminant. Reliable means that the reflectance $\rho$ determined by interpolation depends little on errors related to noises from the source 10 and the sensor 12.

Figure 8:
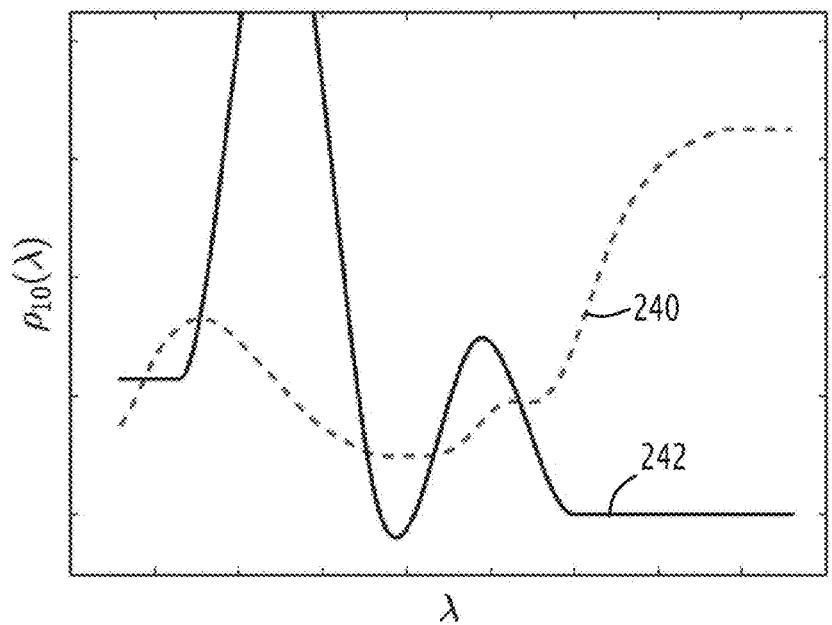
Figure 9:
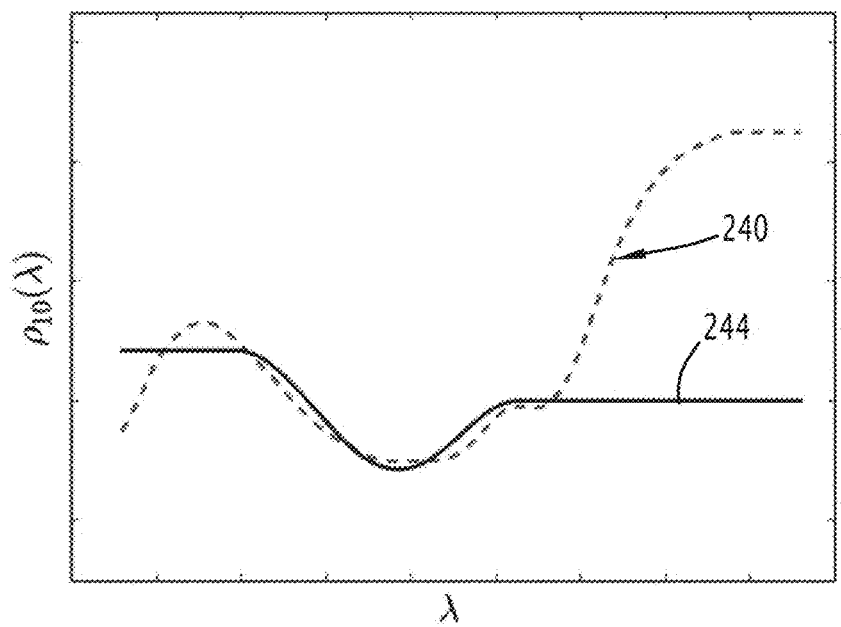

FIGS. 8 and 9 illustrate the advantage of carrying out the determination method by the applicant. In FIGS. 8 and 9, the curve 240 in dotted lines represents the actual reflectance $\rho_{réelle}$ known by other means.

In FIG. 8, the curve in solid lines 242 represents the reflectance determined with the implementation of a method not using the first approximation or the second approximation. In FIG. 9, the curve in solid lines 244 represents the reflectance determined with the implementation of a determination method according to the invention. The analysis of FIGS. 8 and 9 shows that the reflectance determined from the determination method is closer to the actual reflectance $\rho_{réelle}$ than the reflectance determined from the method not using the first approximation or the second approximation.

The third approximation makes it possible to reduce the number of unknowns in the equation to be solved (1).

This results in a better determined reflectance $\rho$ with the same calculation time. The difficulty for the applicant was in selecting an approximation decreasing the calculation time without penalizing the precision of the determined reflectance p.

One specific implementation of the third approximation is outlined below.

Figure 10:
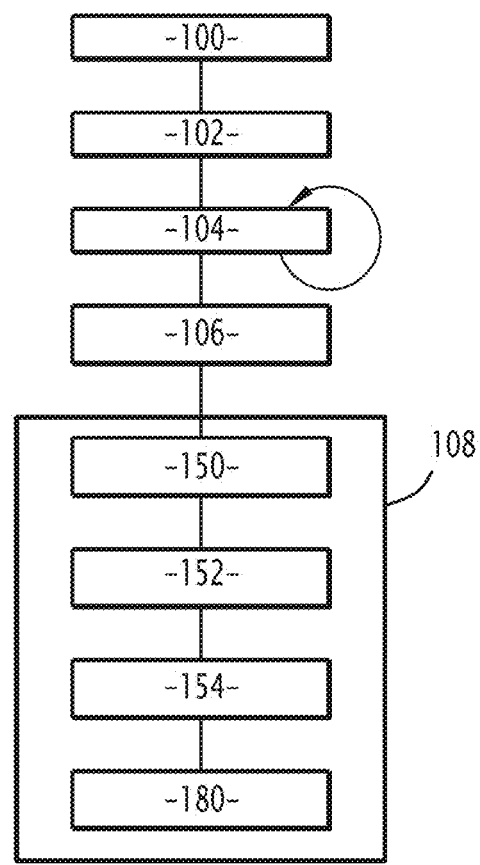

FIG. 10 is a flowchart illustrating one particular implementation of the method for determining the reflectance $\rho$.

The same steps as for the implementation of the method according to FIG. 2 are carried out.

Furthermore, the method includes three additional steps.

According to the first additional step 160, a reference image is taken by the sensor 12 without any flash emitted by the source 10.

Similarly to what has been previously explained, it is possible to deduce an equation therefrom linking the data of the reference image to the spectral behavior of the object 4. Such an equation is called reference equation (4).

The third approximation, according to which the illumination of the outside illuminant 6 at the moment of emission of a flash of light 18 is equal to the illumination of the outside illuminant 6 at a preceding moment, can then be used as follows.

The reference equation (4) provides access to the illumination from the outside illuminant 6. The solving of the equation to be solved (1) is then made easier through an operation for subtraction of the reference equation (4).

This operation eliminates one unknown from the equation to be solved (1), namely the illumination of the outside illuminant 6, which results in a simplified equation.

The first sub-step 150 and the second sub-step 152 are then carried out on the simplified equation.

In the embodiment illustrated in FIG. 10, a second additional step 170 and a third additional step 172 are also carried out.

During the second additional step 170, a variation time interval is estimated for the illumination of the outside illuminant 6.

Such an estimate is for example obtained by comparing a series of images taken by the sensor 12.

During the third additional step 172, a reference image acquisition frequency is determined to ensure that a reference image has been taken in the estimated variation time interval.

For example, the image acquisition frequency is deduced by a numerical relationship of the determined variation time interval.

Such a relationship is for example a proportionality relation.

According to another example, such a relation is a linear relation leading to the setting of a safety margin.

Such an embodiment is easy to carry out, since it suffices to take an additional image. In particular, no additional equipment is used.

In all of the embodiments, the method for determining the reflectance $\rho$ of an object makes it possible to obtain a reliable model of the actual reflectance $\rho$ of the object even with a variable outside illuminant. Reliable means that the reflectance $\rho$ determined by interpolation depends little on errors related to noises from the source 10 and the sensor 12.

In one alternative, the sensor 12 and the source 10 are positioned on different apparatuses 16.

In one alternative, the sensor 12 and the source 10 are positioned on the same apparatus 16 and the processing unit 14 is situated away from the apparatus 16.

Furthermore, it should be noted that the method makes it possible to determine the reflectance of the observed surface for each image point of the sensor 12.

The invention claimed is:

1. A method for determining the reflectance of an object, the method comprising the following steps:
    illuminating the object using an outside illuminant having an unknown and variable illumination,
    emitting at least one flash of light illuminating the object, each flash of light being emitted by a source and having a known illumination in a wavelength range,
    collecting the wave reflected by the object to form at least one image on a sensor,
    obtaining an equation with several unknowns, the equation being obtained from formed images, the reflectance of the object and the illumination of the outside illuminant being two unknowns of the equation,
    solving the equation,
the step for solving the equation comprising
    calculating solution points of the equation,
    interpolating points calculated by an interpolation function, and
    using at least one of the following approximations to solve the equation:
        a first approximation according to which each image is derived from the emission of a separate flash of light,
        a second approximation according to which the interpolation function determines the stability points of the equation, and
        a third approximation according to which the illumination of the outside illuminant at the moment of emission of a flash of light is equal to the illumination of the outside illuminant at a preceding moment.

2. The method according to claim 1, wherein the source and the sensor are positioned on a same apparatus.

3. The method according to claim 1, wherein a plurality of flashes of light are emitted, each flash having maximum wavelength illumination, the collecting step being carried out for each flash of light emitted and at least two flashes of light have a maximum illumination separated by at least 20 nanometers.

4. The method according to claim 1, wherein the collecting step is carried out several times for a same flash of light, the obtained equation being an over-determined system of equations, the solving step being carried out for a plurality of determined equation systems by using the first approximation to obtain a plurality of reflectance functions, the method further comprising calculating the reflectance of the object by calculating a mean of the plurality of reflectance functions.

5. The method according to claim 1, wherein the second approximation is used during the step for solving the equation and in which the interpolation function is a weighted combination of base functions sealed by a finite number of interpolation points, in particular cubic splines, each interpolation point being a stability point of the equation.

6. The method according to claim 5, wherein a plurality of flashes of light are emitted, each flash having maximum wavelength illumination, the collecting step being carried out for each flash of light emitted, and the interpolation points verify at least the following property:
    the number of interpolation points is equal to the number of flashes.

7. A method according to claim 1, wherein the third approximation is used during the step for solving the equation and in which the method comprises a step for taking a reference image by collecting the wave reflected by the object to form at least one image on a sensor in the absence of flash emitted by the source.

8. The method according to claim 7, wherein the step for solving the equation comprises an operation of subtraction of a reference equation to obtain a simplified equation, the reference equation being obtained from the reference image.

9. The method according to claim 7, wherein the method further comprises the following steps:
    estimating a variation time interval for the illumination of the outside illuminant,
    from the estimated variation time interval, determining the frequency at which the step for taking a reference image is to be reiterated in order for the first approximation to remain valid.

10. A device for determining the reflectance of an object, the object being illuminated by an outside illuminant having an unknown and variable illumination, the device comprising:
    a source, able to emit at least one flash of light illuminating the object, each flash of light emitted by the source having a known illumination in a wavelength range,
    a sensor, able to collect the wave reflected by the object to form at least one image,
    a processing unit, able to carry out the following steps:
        obtaining an equation with several unknowns, the equation being obtained from formed images, the reflectance of the object and the illumination of the outside illuminant being two unknowns of the equation,
        solving the equation,
    the step for solving the equation comprising:
        calculating solution points of the equation,
        interpolating points calculated by an interpolation function, and
        using at least one of the following approximations to solve the equation:
            a first approximation according to which each image is derived from the emission of a separate flash of light,
            a second approximation according to which the interpolation function determines the stability points of the equation, and a third approximation according to which the illumination of the outside illuminant at the moment of emission of a flash of light is equal to the illumination of the outside illuminant at a preceding moment.

11. The device according to claim 10, wherein the sensor and the source are positioned on a same apparatus.

12. The device according to claim 10, wherein the source is a light screen or a set of light-emitting diodes.

13. The device according to claim 10, wherein the sensor is chosen from a group made up of a photographic camera, a camera, a multichannel imager and a hyperspectral imager.

* * * * *